United States Patent [19]
Koch et al.

[11] Patent Number: 5,236,459
[45] Date of Patent: Aug. 17, 1993

[54] BONE IMPLANT AND METHOD OF MAKING SAME

[75] Inventors: Rudolf Koch, Berlingen; Urs Wehrle, Frauenfeld, both of Switzerland

[73] Assignee: Sulzer Brothers Limited, Winterthur, Switzerland

[21] Appl. No.: 937,929

[22] Filed: Aug. 31, 1992

Related U.S. Application Data

[62] Division of Ser. No. 570,909, Aug. 22, 1990, Pat. No. 5,171,327.

[30] Foreign Application Priority Data

Sep. 6, 1989 [CH] Switzerland ............... 3239/89

[51] Int. Cl.$^5$ .................. A61F 2/02; A61F 2/28; A61F 2/30; B26F 3/00
[52] U.S. Cl. ...................... 623/16; 623/11; 623/18; 623/66; 83/177; 51/319

[58] Field of Search .............. 623/11, 12, 16, 18, 623/20, 23, 66, 1; 606/62; 83/177, 53; 51/319, 320, 321

[56] References Cited

U.S. PATENT DOCUMENTS

5,097,731  3/1992  Vives et al. ............... 83/177 X
5,161,305  11/1992  Yamakawa ............... 83/177 X

*Primary Examiner*—Randall L. Green
*Assistant Examiner*—Dinh X. Nguyen
*Attorney, Agent, or Firm*—Kenyon & Kenyon

[57] ABSTRACT

A bone implant is provided with undercut anchoring areas for bone tissue which extend from the surface of the implant into the interior. Geometrically shaped cavities are generated through the openings in an interconnected manner to provide for the ingrowth of bone tissue. A high pressure liquid jet is used to form the cone-shaped cavities in the implant on spacings to provide for intercommunication between the respective cavities.

3 Claims, 2 Drawing Sheets

BONE IMPLANT AND METHOD OF MAKING SAME

This application is a division of application Ser. No. 07/570,909, filed on Aug. 22, 1990 now U.S. Pat. No. 5,171,327 issued Dec. 15, 1992.

This invention relates to a bone implant and to a method of making the same. More particularly, this invention relates to a bone implant having anchoring areas for bone tissue and to a method of generating anchoring areas on an implant.

Heretofore, in the case of implants which are to be implanted in the human body, the practice is known of making the surfaces of the implants porous or of coating the implants with metallic grids in order to facilitate the ingrowth of tissue. For example, German AS 24 04 214 which corresponds to U.S. Pat. No. 3,905,777, describes various arrangements in which one or more layers of a metal grid, preferably formed of expanded metal, are welded to the core of the body of the implant. Similarly, Swiss Patent 665,348 describes a coating for implants which consists of a number of metal grids in layers, one above the other and connected together. In this case, the mesh width decreases from one layer to the next in the direction towards the interior of the implant. The purpose of such constructions is to bring about a growth of bone tissue into the implant which is as satisfactory as possible.

However, it has proved disadvantageous and restrictive to have the grids made of metal and to require attachment of the grids, for example, by spot-welding to the implant or to the bearer body. First, this restricts the application to metal bearer bodies and second, during manufacture, local high temperatures arise which involve modifications in structure and chemical reactions with the ambient. These, in turn, have an unfavorable effect upon compatibility with the human body.

French Patent 2,350,827 describes an implant which is provided with a plastic layer having imbedded particles of a mixture $CaO:P_2O_5 = 3:4$. The particles are biodegradable after implantation and leave cavities for the ingrowth of bone tissue, the shape of the cavities corresponding to the shape of the particles and their common contacting surfaces.

W086/02824 describes an element for controlled growth of tissue, for example around teeth. In this respect, the element is provided with a number of internal cavities in an external wall and circumferential slots which communicate with the internal cavities. In addition, opening are provided adjacent to the slots to communicate with each internal cavity.

European Patent Application 0162604 describes an implant having an integral attachment surface including a plurality of upstanding posts arranged within a grid of crossing channels or groups. It is proposed to generate the surface by machining with a laser beam, which might reduce the strength of the material at the surface and which might also cause unfavourable chemical reactions with the atmosphere.

German OS33 30 671 describes an implant having a plurality of circular grooves with projecting posts in the center of the grooves. Likewise, German OS31 19 130 describes an implant having a surface provided with semi-circular depressions and apertures at the bases of the depressions in order to provide an anchorage surface.

French Patent 2,433,336 describes an implant having a plastic structure formed with an irregular external surface.

Accordingly, it is an object of the invention to provide a bone implant with interconnected internal cavities for the ingrowth of bone tissue.

It is another object of the invention to create an anchoring area on an implant for the ingrowth of bone tissue which does not require a separately applied grid.

It is another boject of the invention to provide an anchoring area for bone tissue on a bone implant which does not exhibit sharp edges.

Briefly, the invention provides bone implant which is comprised of a body having an external surface for facing bone tissue and a plurality of geometrically shaped cavities below the surface and disposed in a grid. In addition, each cavity has an opening in the surface of the body and continues into an adjacent cavity below the surface of the body.

The bone implant has the advantage that, independent of the kind of material of the implant and without melting action or chemical reactions, the anchoring areas provided by the cavities are generated with smooth rounded transitions.

With the apertures communicating below the surface of the implant, the tissue which subsequently grows into the cavities can be nourished via a plurality of supply openings. This reduces the risk of necrosis of the tissue due to microscopic shiftings of the implant.

The invention also provides a method of generating anchoring areas on an implant which includes the steps of directing a high pressure liquid jet against a body on an axis perpendicular to a surface of the body in order to form an opening in the surface. Thereafter, the jet is directed through the opening on an angle relative to the perpendicular axis while being rotated on a circular motion about the axis in order to form a cavity within the body below the surface. In this respect, the high pressure liquid jet is one which is limited in its depth of action. In addition, abrasive biocompatible particles are mixed into the jet in order to form the opening and the cavities within a surface of a bone implant.

These and other objects and advantages of the invention will become more apparent from the following detailed description taken in conjunction with the accompanying drawings wherein.

Figure 1:
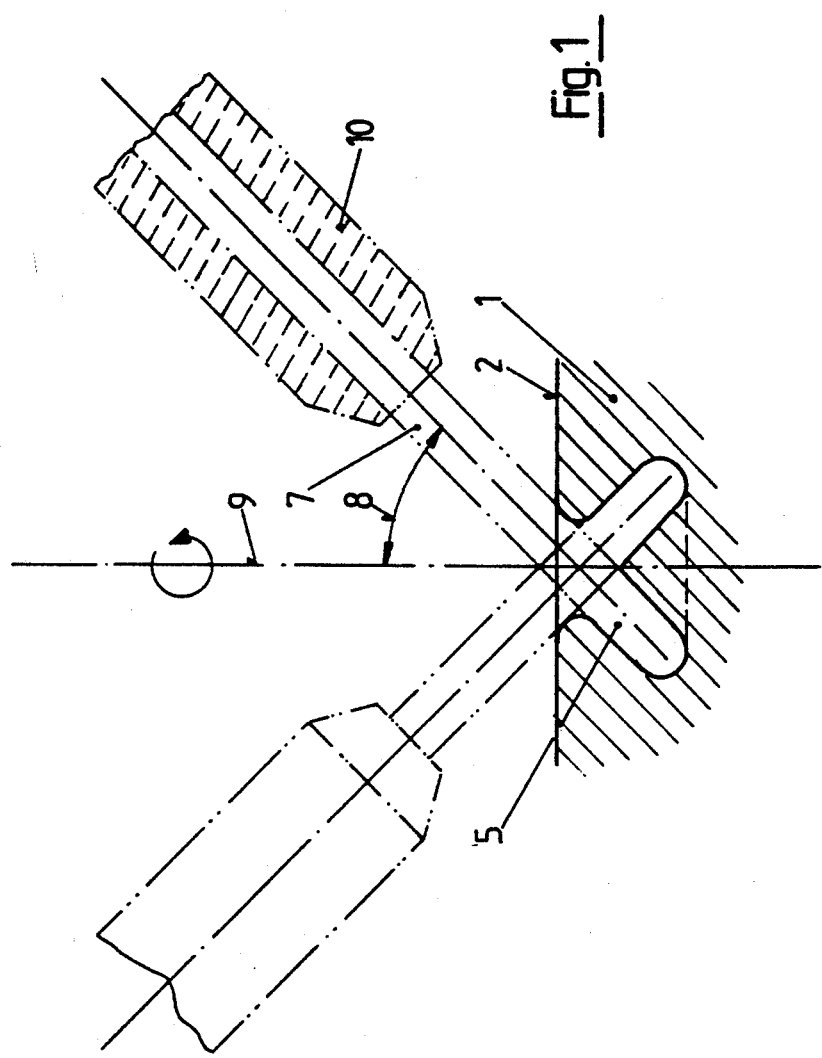
FIG. 1 illustrates a part cross-sectional view of an implant during generation of an anchoring area in accordance with the invention.
Figure 2:
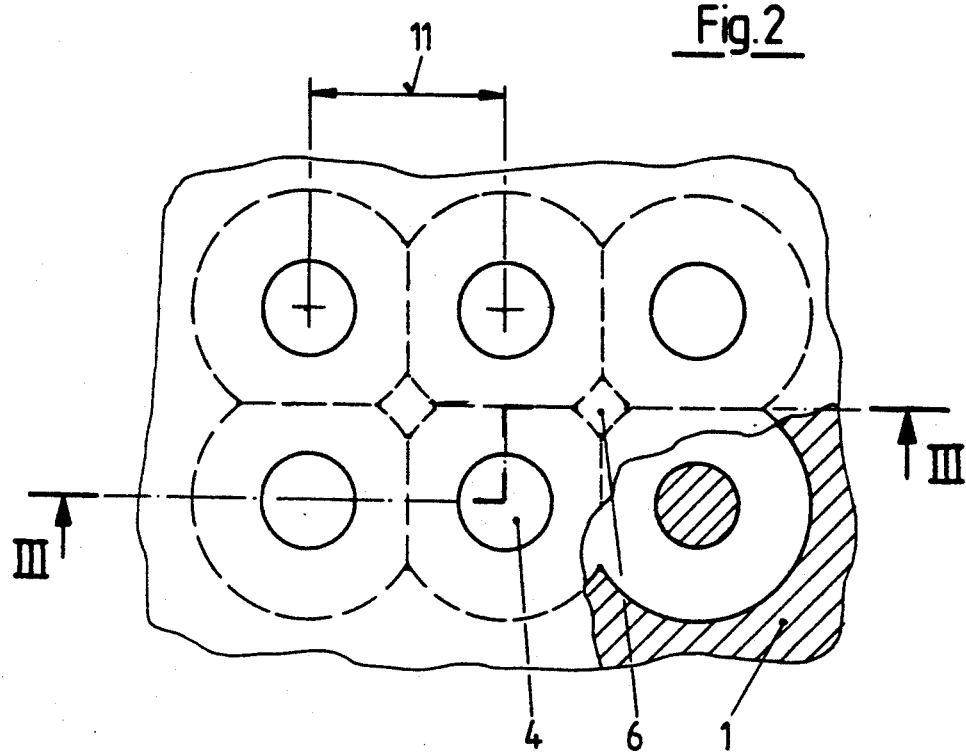
FIG. 2 illustrates a plan view of a machined area of an implant having a plurality of anchoring areas below a surface of the implant in accordance with the invention.

Referring to FIG. 1, the implant 1 is comprised of a body having an external surface 2 for facing bone tissue (not shown) In addition, the body 1 has a plurality of geometrically shaped cavities 5 below the surface 2, as viewed, which are disposed in a grid as indicated in FIG. 2.

Figure 3:
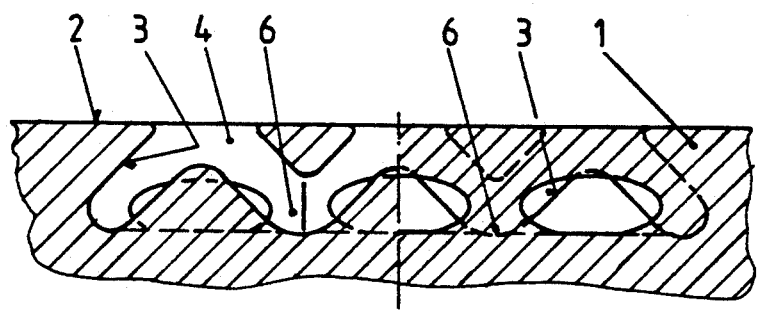
FIG. 3 illustrates a view taken on line III—III of FIG. 2.

Referring to FIGS. 2 and 3, each cavity 5 has an opening 4 in the surface 2 of the body and continues into an adjacent cavity below the surface 2. As indicated in FIG. 1, each cavity 5 is defined in part by a conical wall and an upstanding a central portion of conical shape disposed on a central axis of the cavity each cavity 5 also has a rounded transition portion about the opening 4.

As illustrated in FIGS. 2 and 3, a plurality of supporting column 6 are disposed between the cavities 5 with each column 6 extending from the surface 2 of the body 1 between four adjacent cavities 5. As indicated in FIG. 2, the cavities 5 are disposed on a rectangular grid with the openings 4 of the cavity as well as the cavities being equispaced from the other. In addition, each cavity 5 has a center line spaced from a center line of an adjacent cavity a distance 11 greater than a diameter of the opening 4 therein and less than the diameter of the base of the cavity within the body 1.

As indicated in FIGS. 2 and 3, the openings 4 are spaced apart on the body 1 while the cavities 5 overlap each other within the body 1, that is, below the external surface 2. In this way, the cavities 5 provide for the ingrowth of bone tissue via the openings 4. At the same time, the cavities communicate with each other through anchoring areas or openings 3 so that bone tissue may grow therethrough. The openings 4 thus serve to provide for nourishment of the bone tissue which grows into each cavity 5 and from each cavity 5 into an adjacent cavity 5 through the openings therebetween.

Referring to FIG. 1, in order to form the cavities in the implant for bone anchorage purposes, a high pressure liquid jet 7 which is limited in its depth of action and into which abrasive particles compatible with the human body are mixed is directed against the surface 2 of the implant 1 on an axis 9 perpendicular to the surface 2 of the body 1 in order to form an opening 4 in the surface 2. As indicated, the jet 7 is guided by means of an outlet nozzle 10. By setting the high pressure liquid jet 7 on the perpendicular axis 9, a blind hole is first of all generated, that is, the opening which is to form the opening 4 to a cavity 5. Thereafter, the jet is directed through the opening on a generatrix to form a cavity below the surface. To this end, the jet 7 is disposed on an angle of attack 8 relative to the axis 9 while being rotated on a circular motion about the axis 9 in order to form a cavity having a cone-shape within the body 1 below the surface 2.

Thereafter, the jet 7 can be directed on a new perpendicular axis spaced from the first perpendicular axis by a distance greater than the diameter of the aperture 4 but smaller than the diameter of the base of the cone-shaped cavity 5. In this way, a series of cavities can be formed in the implant body 1. As indicated in FIG. 3, the adjacent cone-shaped cavities 5 penetrate into one another in a mutual manner below the surface 2 of the implant. By a skillful choice of the pitch 11 between adjacent shaped cavities and through the arrangement in a grid pattern, whole areas may be hollowed out in the form of a vault which exhibits a supporting column 6 and openings through to the surface 2.

After the production of the final surface 2 of an implant as a reference area, the generation of the anchoring areas may be performed at any time. In this respect, there must merely be adequate possibilities of clamping the implant in order to absorb the forces of reaction generated by the high pressure jet 7.

The implant may be made of a material selected from the group consisting of metal, ceramic and carbon as well as of compound materials.

The invention thus provides a bone implant with integrated anchorage areas for the ingrowth of bone tissue below a surface of the implant. In this respect, the bone implant does not require the welding on of metal grids, the spraying on of metallic coatings or otherwise or any other technique which requires heating of the substrate.

The invention further provides an implant with communicating cavities below the surface of the implant to provide anchorage areas for the ingrowth of bone tissue so as to provide for improved anchorage in a bone while at the same time providing for nourishment of the bone tissue which grows into the cavities.

The preferred parameter of the equipment are: A liquid jet of normal clean water. It is formed in a nozzle with a differential pressure up to 4000 bar. The diameter of the nozzle can vary from 0.1 to 2 mm. Abrasive particles can be added to the liquid if their diameter is about 8 times s smaller than the smallest inside diameter of the nozzle. However, plastic material is machined by a pure water jet. For a given size of nozzle at a suitable distance to the machined surface the main parameters are the differential pressure at the nozzle and the exposing time of the surface.

Typical data to produce internal interconnected cavities in a titanium body are:
inside diameter of the nozzle 0.75 mm;
abrasive particles added: corundum (trade name OLIVIN-SAND) with grain size 90 μm;
differential pressure over the nozzle: 2200 bar;
by variation of pressure and of exposing time the diameter of the cavities at the surface can be varied from 0.5 to 1.5 mm which is judged to be a suitable size for the ingrowth of bone tissue.

What is claimed is:

1. A method of generating anchoring areas on an implant comprising the steps of
providing a bone implant body;
directing a high pressure liquid jet against said bone implant body on an axis perpendicular to a surface of said bone implant body to form an opening in said surface; and
thereafter directing said jet through said opening on an angle relative to said axis while rotating said jet on a circular motion about said axis to form a cavity within the body below said surface.

2. A method as set forth in claim 1 wherein a multiplicity of said openings and said cavities are formed in a grid pattern in said body.

3. A method as set forth in claim 2 which further comprises the step of mixing abrasive biocompatible particles into said jet to form said openings and said cavities.

* * * * *

UNITED STATES PATENT AND TRADEMARK OFFICE
CERTIFICATE OF CORRECTION

PATENT NO. : 5,236,459

DATED : August 17, 1993

INVENTOR(S) : Koch et al.

It is certified that error appears in the above-identified patent and that said Letters Patent is hereby corrected as shown below:

Column 2, line 68, change "cavity each" to --cavity.
Each--;

Column 3, line 4, change "column" to --columns--;
line 40, change "on" to --in--; and Column 4 line 24, delete "s".

Signed and Sealed this

Thirteenth Day of September, 1994

Attest:

BRUCE LEHMAN

Attesting Officer       Commissioner of Patents and Trademarks